(12) United States Patent
Chen

(10) Patent No.: US 7,229,416 B2
(45) Date of Patent: Jun. 12, 2007

(54) EXERCISE EXPENDITURE MONITOR DEVICE AND METHOD

(76) Inventor: Yu-yu Chen, 2 Fl., No. 349, Wushing St., Shinyi Chiu, Taipei (TW) 110

( * ) Notice: Subject to any disclaimer, the term of this patent is extended or adjusted under 35 U.S.C. 154(b) by 0 days.

(21) Appl. No.: 10/747,356

(22) Filed: Dec. 30, 2003

(65) Prior Publication Data

US 2005/0148827 A1 Jul. 7, 2005

(51) Int. Cl.
*A61B 5/02* (2006.01)
*A63B 71/00* (2006.01)

(52) U.S. Cl. ............... 600/500; 600/503; 482/8

(58) Field of Classification Search ........ 600/500–503, 600/520, 300, 301; 128/920–925; 482/8
See application file for complete search history.

(56) References Cited

U.S. PATENT DOCUMENTS

| | | | |
|---|---|---|---|
| 4,367,752 A * | 1/1983 | Jimenez et al. | 600/502 |
| 4,434,801 A * | 3/1984 | Jiminez et al. | 600/502 |
| 4,566,461 A * | 1/1986 | Lubell et al. | 600/481 |
| 6,013,009 A * | 1/2000 | Karkanen | 482/9 |
| 6,537,227 B2 * | 3/2003 | Kinnunen et al. | 600/500 |
| 6,540,686 B2 * | 4/2003 | Heikkila et al. | 600/483 |
| 6,605,044 B2 * | 8/2003 | Bimbaum | 600/500 |
| 6,675,041 B2 * | 1/2004 | Dickinson | 600/509 |
| 6,808,473 B2 * | 10/2004 | Hisano et al. | 482/8 |
| 2001/0023320 A1 * | 9/2001 | Kinnunen et al. | 600/500 |

* cited by examiner

Primary Examiner—Robert L. Nasser
Assistant Examiner—Navin Natnithithadha
(74) Attorney, Agent, or Firm—Rosenberg, Klein & Lee

(57) ABSTRACT

An exercise expenditure monitor device and method for monitoring a user's caloric expenditure at exercise, the exercise expenditure monitor device including a heartbeat sensing device for detecting heart rate of the user, a reference storage unit for storing a standard heart rate and a reference heart rate of the user at rest mode, an individual physiology database for storing data of physiology weighted value and a set of individual physiological parameters inputted by the user including sex, age and weight, each set of individual physiological parameters corresponding to a physiology weighted value, a calculating unit which calculates a general caloric expenditure of the user according to an algorithm including dividing the heart rate difference between the exercise heart rate and the reference heart rate by the reference heart rate and multiplying by the physiology weighted value. Preferably, the exercise expenditure monitoring device includes an activity mode selection unit for storing data of activity weighted value and the item of activity that the user takes e.g. walking, jogging, running, jumping, cycling or aerobic dance. Each activity corresponds to an activity weighted value which is provided to the calculating unit which multiplies the general caloric expenditure by the activity weighted value and obtains a true caloric expenditure of the user.

12 Claims, 4 Drawing Sheets

EXERCISE EXPENDITURE MONITOR DEVICE AND METHOD

BACKGROUND OF THE INVENTION

1. Field of the Invention

The present invention relates to an exercise monitor, and more particularly to an exercise expenditure monitor device and method for monitoring a user's caloric expenditure at exercise.

2. Description of the Prior Art

In the modern society, people have been living and working busily. They are inevitably always under substantial pressure. To relief pressure and for the sake of health, many people do exercise during spare time. Most people have their favorite sports and exercises. Some people prefer simple exercises like walking, jogging, running, jumping, hiking, and so on, and some people like to do exercise with exercise equipment.

Usually, when a user do exercise, he wants to measure and control the amount of exercise he takes. There are a variety of body building devices and exercisers in the market. However, the exercise equipment early developed can only provide simple functions for exercising, and are not capable to measure the amount of calorie that the user consumes. Hence, it is not easy for the exerciser to control an appropriate amount of exercise.

There are various types of body/motion signal sensing devices for a person to measure the amount of exercise taken and to monitor his personal physical conditions e.g. pedometer and heartbeat sensing device. However, most body signal sensing devices or motion signal sensing devices are only able to detect and indicate simple data. For example, a conventional pedometer can only measure the accumulated steps taken, and a conventional heartbeat sensing device can only detect the heartbeats of the user.

In U.S. Pat. No. 5,491,474, a telemetric transmitter unit is disclosed. The transmitter electronics is coupled to each electrode by means of a conductive plastic layer for transmission of signal. In U.S. Pat. No. 4,513,753, a heartbeat rate indicator in the form of a wristwatch is disclosed. Moreover, U.S. Pat. No. 5,622,180 describes a device for measuring heartbeat rate that includes a wrist strap with skin contact electrodes and a coil receiver for receiving telemetrically transmitted heartbeat signals either from a wireless receiver or from the skin contact electrodes.

Also, U.S. Pat. Nos. 4,371,945 and 5,164,967 disclose a pedometer for calculating a distance which a user walks, jogs or runs by electronically measuring the length of each stride taken by the use.

All of the aforesaid conventional body signal sensing devices and motion signal sensing devices are designed to have only one detecting and sensing function. That is, in practical use of these conventional sensing devices, they can detect and display only one type of signal. Body signal, for example heartbeat rate, if it is evaluated together with the exercise intensity, exercise type or exercise parameter, it is very useful and beneficial for athletes and sports fans. In fact, most of the products in market do not match the requirements in practical way.

Some producers have devoted to develop a few body signal sensing devices with multiple functions. Take for an example. U.S. Pat. No. 5,891,042 discloses a fitness monitoring device that includes an electronic pedometer which responds to a user's body motion at each step and a wireless heart rate monitor which is wirelessly coupled to the electronic pedometer. The pedometer is fitted to the user's waist and the wireless heartbeat monitoring device is fitted to the user's chest. The heartbeat signal is transmitted wirelessly to and is displayed on the pedometer. Practically, it is not easy and inconvenient for the user to view the data displayed on the pedometer.

Also, exercise monitors with calculating unit are known. Such exercise monitors are improved with expanded functions and are capable to measure the quantity of exercise. U.S. Pat. No. 6,605,044 discloses a caloric exercise monitor that is able to display either or both the calories remaining to be expended to reach the entered goal or the remaining exercise time required to reach the entered goal on a display. However, the calorie exercise monitoring device is not practical.

SUMMARY OF THE INVENTION

Thus, a primary object of the present invention is to provide an exercise expenditure monitor device capable of providing a caloric expenditure of a user at exercise based on the user's heart rate detected.

Another object of the present invention is to provide an exercise expenditure monitor device capable of providing the caloric expenditure of the user at exercise based on his individual physiological parameters e.g. age, sex and weight and the item of activity that the user performs.

A further object of the invention is to provide an exercise expenditure monitor method which can calculate the user's caloric expenditure from the heart rate difference between exercise heart rate and reference heart rate at rest mode, the individual physiological parameters and the item of activity that the user performs.

To achieve the above and other objects, in accordance with the present invention, there is provided with an exercise expenditure monitor device and a method for monitoring a user's caloric expenditure at exercise. The exercise expenditure monitor device includes a heartbeat sensing device for detecting at least a heart rate of the user at exercise, a reference storage unit for storing a standard heart rate and a reference heart rate of the user at rest mode, an individual physiology database for storing a data of physiology weighted values and a set of individual physiological parameters inputted by the user including sex, age and weight, each set of individual physiological parameters corresponding to a physiology weighted value, a calculating unit which calculates a general caloric expenditure of the user according to an algorithm including dividing the heart rate difference between the exercise heart rate and the reference heart rate by the reference heart rate and multiplying by the physiology weighted value.

Preferably, the exercise expenditure monitoring device further includes an activity mode selection unit for storing data of activity weighted values and the item of activity that the user takes e.g. walking, jogging, running, jumping, cycling or aerobic dance. Each activity corresponds to an activity weighted value which is provided to the calculating unit that further multiplies the general caloric expenditure by the activity weighted value and obtains a true caloric expenditure of the user.

BRIEF DESCRIPTION OF THE DRAWINGS

The present invention will be apparent to those skilled in the art by reading the following description of the best mode and a preferred embodiment of a device for carrying out the present invention, with reference to the attached drawings, in which.

DETAILED DESCRIPTION OF THE PREFERRED EMBODIMENTS

Figure 1:
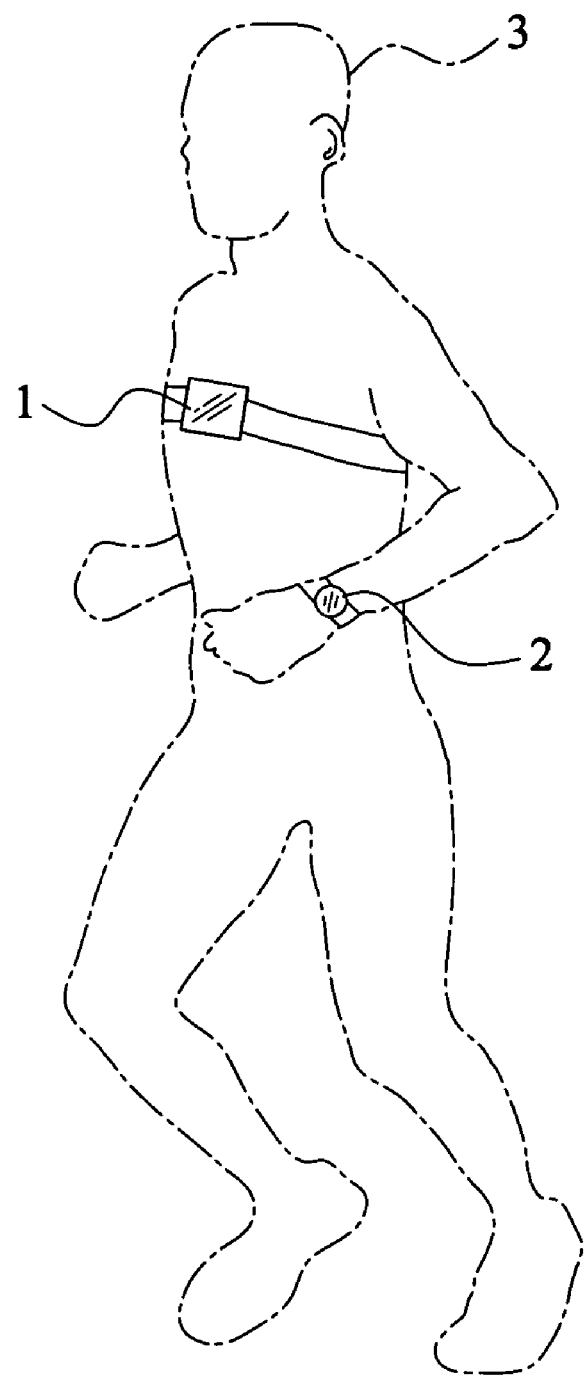
FIG. 1 is a perspective view showing that an exercise expenditure monitor device constructed according to the present invention is fitted to a user.
Figure 2:
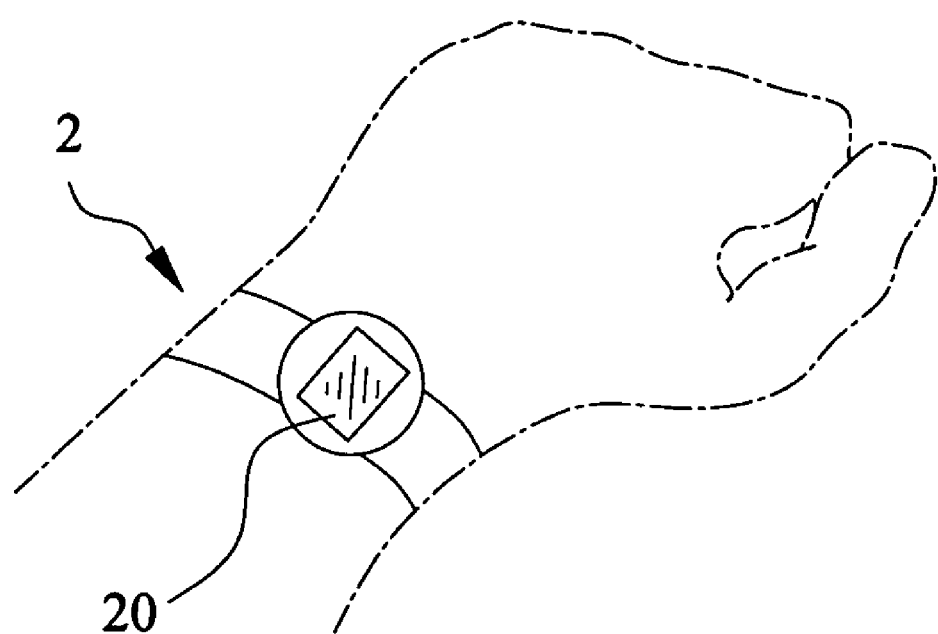
FIG. 2 is perspective view showing that a monitoring device of the exercise expenditure monitor device is fitted to a wrist of the user.

With reference to the drawings and in particular to FIG. 1 which is a perspective view showing that an exercise expenditure monitor device of the present invention is fitted to a user. The exercise expenditure monitor device of the present invention comprises a wireless heartbeat sensing device 1 and a monitoring device 2. Please also refer to FIG. 2. The wireless heartbeat sensing device 1 is fitted to a chest of the user 3 for detecting at least a heart rate of the user, and the monitoring device 2 is fitted to a wrist of the user for displaying. It should be understood that the monitoring device may be positioned on any place e.g. on an exercise equipment that is convenient for the user to view and is not limited to be put on the wrist of the user.

Figure 3:
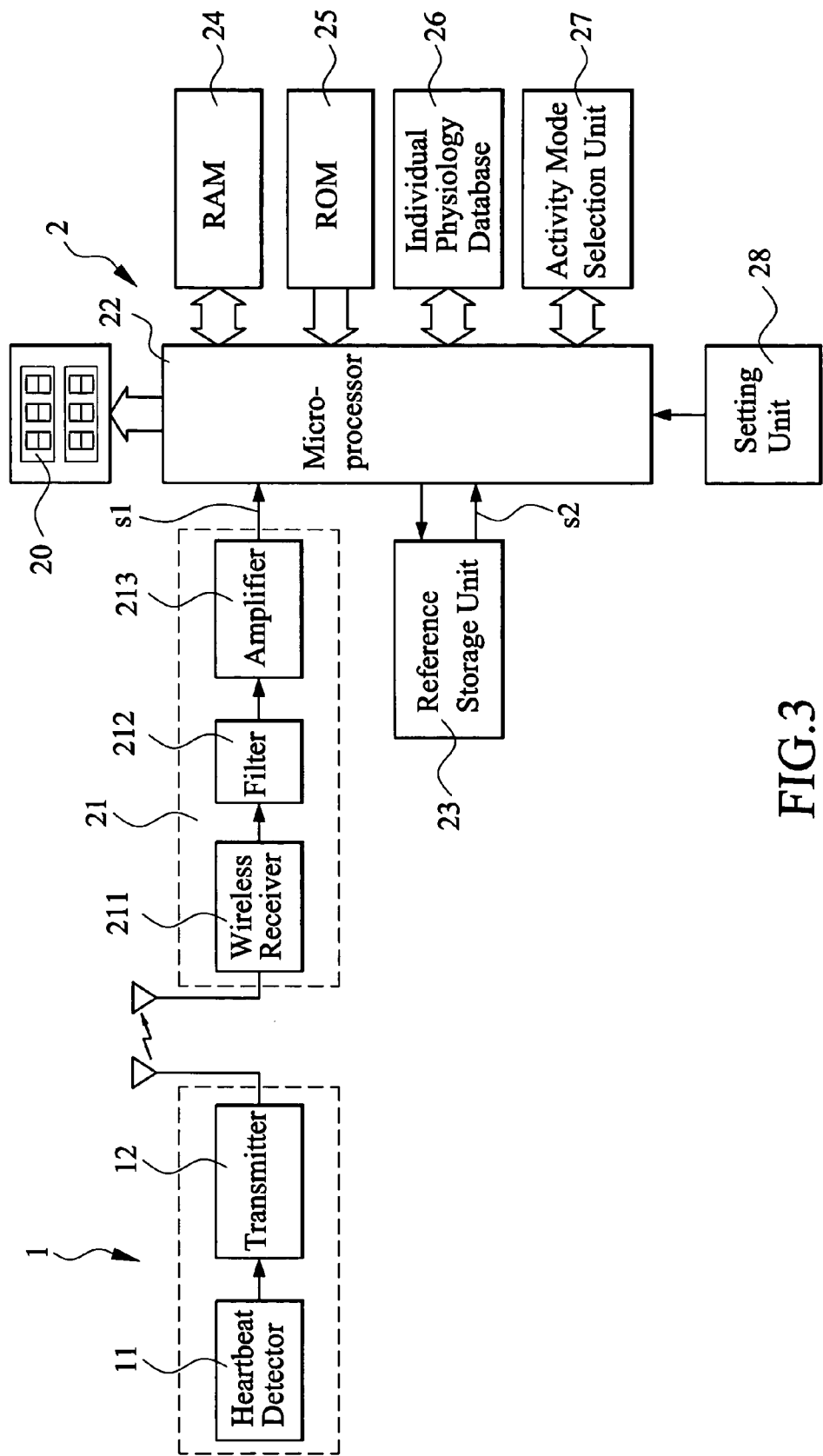
FIG. 3 is a block diagram showing a control circuit of the exercise expenditure monitor device in accordance with a preferred embodiment of the present invention.

As shown in FIG. 3 which is a block diagram of a control circuit of the exercise expenditure monitor device in accordance with a preferred embodiment of the invention, the wireless heartbeat sensing device 1 comprises a heartbeat detector 11 and a wireless transmitter 12. The heartbeat detector 11 detects a heart rate of the user and forwards a heartbeat signal to the wireless transmitter 12 which transmits the heartbeat signal wirelessly.

The monitoring device 2 comprises a wireless receiving circuit 21 for receiving the heartbeat signal transmitted by the wireless heartbeat sensing device 1. The wireless receiving circuit 21 comprises a wireless receiver 211 for receiving the heartbeat signal wirelessly and transmitting the heartbeat signal to a filter 212 for filtering the noise. The filtered heartbeat signal is then transmitted to an amplifier 213 for amplifying. Subsequently, the amplified heartbeat signal s1 is transmitted to a calculating unit for calculating and processing. The calculating unit may be comprised of a microprocessor 22.

The microprocessor 22 is connected with a reference storage unit 23 which stores and provides a reference heart rate s2 to the microprocessor 22. The reference heart rate s2 can be either a standard heart rate or a resting heart rate of the user. The user's resting heart rate is either inputted by the user or provided by the heartbeat sensing device 1 which detects the heart rate of the user at rest status and transmits the heartbeat signal wirelessly via the wireless receiving circuit 21 to the reference storage unit 23 for storing.

The microprocessor 22 is coupled to a random access memory (RAM) 24 and a read only memory (ROM) 25. The RAM 24 comprises a memory for temporary storage of data for the microprocessor during operation of the exercise expenditure monitor device. The ROM 25 stores the operation program of the exercise expenditure monitor device.

The microprocessor 22 is also coupled with an individual physiology database 26 which stores the individual physiological parameters of the user including sex, age, weight and so on. The individual physiology database 26 also stores a data of physiology weighted value $\alpha$. Each set of the individual physiological parameters corresponds to a physiology weighted value $\alpha$ which is a conversion factor for converting the caloric expenditure from the heart rate.

Moreover, the microprocessor 22 is connected with an activity mode selection unit 27 which stores a data of activity weighted values f and the item of activity inputted by the user. Each activity corresponds to an activity weighted value f. The activity may include walking, jogging, jumping, running, aerobic dance, cycling, and so on.

A setting unit 28 is connected to the microprocessor 22 for inputting data or parameters. The data or parameters may include the reference heart rate, individual physiological parameters and the item of activity, that are then forwarded to the reference storage unit 23, the individual physiology database 26 and the activity mode selection unit 27.

Figure 4:
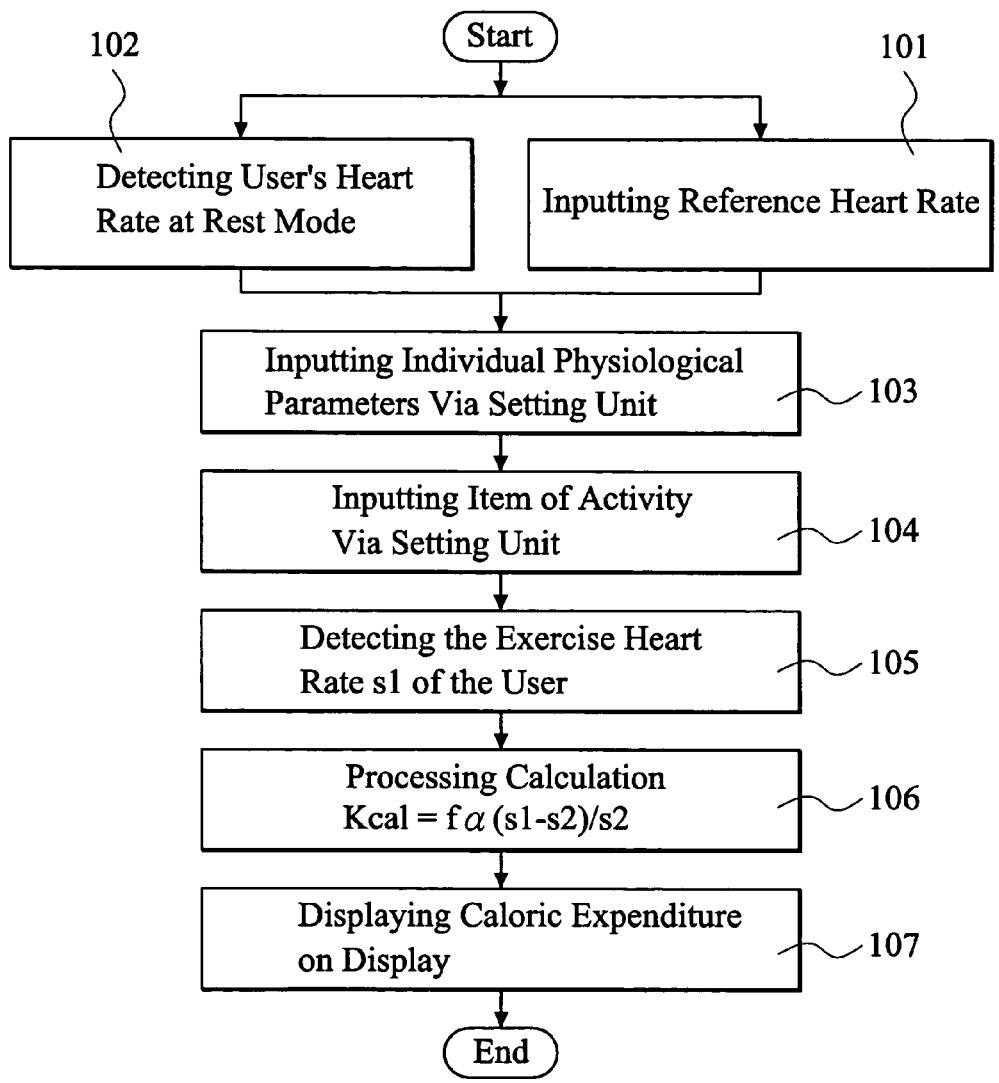
FIG. 4 is a flow chart showing the steps performed during the application of the exercise expenditure monitor device.

Please refer to FIGS. 3 and 4. FIG. 4 is a flowchart showing the steps performed during the application of the exercise expenditure monitor device. Firstly, the user inputs the reference heart rate via the setting unit 28. The reference heart rate is the resting heart rate of the user known by the user (step 101) or detected by the heartbeat sensing device 1 at rest mode (step 102). The reference heart rate is stored in the reference storage unit 23, so that the reference storage unit 23 may supply the reference heart rate s2 to the microprocessor 22.

In the case when the exercise expenditure monitor device does not get the reference heart rate from the user, the reference storage unit 23 provides a standard reference heart rate s2 to the microprocessor 22.

In step 103, the user inputs his individual physiological parameters via the setting unit 28. The individual physiological parameters include sex, age, and weight that are stored in the individual physiology database 26. The individual physiology database 26 provides a physiology weight value $\alpha$ corresponding to the setting of individual physiological parameters. The physiology weighted value $\alpha$ is a conversion factor for converting the caloric expenditure from the heart rate for an individual possessing the physiological characteristics.

In step 104, the user inputs the item of activity that he performs via the setting unit 28, e.g. walking, jogging, jumping, running or aerobic dance. The item of activity is stored in the activity mode selection unit 27. The activity mode selection unit 27 provides an activity weighted value f corresponding to the activity.

The user starts to exercise after the aforesaid steps. The heartbeat sensing device 1 detects the exercise heart rate s1 of the user in step 105. The exercise heart rate s1 is transmitted via the receiving circuit 21 to the microprocessor 22. In step 106, the microprocessor 22 processes calculation. First, a heart rate difference is obtained by subtracting the reference heart rate s2 from the exercise heart rate s1, i.e. (s1–s2). The heart rate difference (s1–s2) is divided by the reference heart rate s2 and multiplied by the physiology weighted value $\alpha$ and the activity weighted value f. The value resulted from the calculation is the caloric expenditure of the user. The caloric expenditure represents the energy in Kcal that the user is expended at taking the activity. In other words, $$\text{Caloric expenditure }(K\text{cal}) = f\alpha(s1-s2)/s2$$

The caloric expenditure is displayed on the display 20 of the monitoring device 2 (step 107). Practically, it is quite simple for the user to use the exercise expenditure monitor device. He just has to fasten the monitoring device 2 on his wrist and fit the heartbeat sensing device 1 to his chest. When the user exercises, the heartbeat sensing device 1 detects his heart rate at exercise, and then the microprocessor processes and calculates. He can easily monitor his caloric expenditure from the display 20 on the monitoring device 2. Accordingly, he can stop exercise when he has consumed an appropriate amount of energy.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. An exercise expenditure monitor device for measuring a caloric expenditure of a user comprising:
   a heartbeat sensing device for detecting at least a heart rate of the user at exercise;
   a reference storage unit for storing a reference heart rate of the user before doing exercise;
   an individual physiology database for storing a data of physiology weighted value and a set of individual physiological parameters inputted by the user including sex, age and weight, in which one set of personal physiological parameters corresponds to a physiology weighted value which is a conversion factor for converting caloric expenditure from the heart rate;
   a calculating unit for processing and calculating a general caloric expenditure of the user according to an algorithm which includes dividing the heart rate difference between the exercise heart rate and the reference heart rate by the reference heart rate and multiplying by the physiology weighted value; and
   a display for displaying the caloric expenditure calculated by the calculating unit.

2. The exercise expenditure monitor device as claimed in claim 1, further comprising an activity mode selection unit which stores a data of activity weighted values and the item of activity inputted by the user, in which each activity corresponds to an activity weighted value, and the calculating unit further multiplies the general caloric expenditure by the activity weighted value, making a true caloric expenditure.

3. The exercise expenditure monitor device as claimed in claim 2, wherein the items of activity include walking, jogging, running, jumping, hiking, aerobic dance and cycling.

4. The exercise expenditure monitor device as claimed in claim 1, wherein the display further displays the exercise heart rate of the user.

5. The exercise expenditure monitor device as claimed in claim 1, wherein the display further displays the individual physiological parameters inputted by the user including sex, age and weight.

6. The exercise expenditure monitor device as claimed in claim 1, wherein the heartbeat sensing device is a wireless heartbeat sensing device which is fitted to the chest of the user for detecting the heart rate of the user.

7. The exercise expenditure monitor device as claimed in claim 1, wherein the monitoring device comprises a monitor for fastening to the wrist of the user.

8. A method for monitoring a caloric expenditure of a user during exercise, comprising the steps of:
   (a) inputting a reference heart rate;
   (b) inputting a set of individual physiological parameters of the user including sex, age and weight;
   (c) detecting the exercise heart rate of the user at exercise;
   (d) calculating a heart rate difference by subtracting the reference heart rate from the exercise heart rate;
   (e) dividing the heart rate difference by the reference heart rate and multiplying by a physiology weighted value, getting a general caloric expenditure of the user; and
   (f) displaying the caloric expenditure.

9. The method as claimed in claim 8, wherein the reference heart rate of step (a) is a standard heart rate.

10. The method as claimed in claim 8, wherein the reference heart rate of step (a) is a resting heart rate of the user inputted by the user.

11. The method as claimed in claim 8, wherein the reference heart rate of step (a) is a heart rate of the user at rest mode detected by the heartbeat sensing device.

12. The method as claimed in claim 8, further comprising a step of inputting an item of activity that the user takes after step (b), each activity corresponding to an activity weighted value which is incorporated in the calculation algorithm by multiplying the general caloric expenditure by the activity weighted value and making a true caloric expenditure of the user.

* * * * *